United States Patent [19]

Buxton et al.

[11] Patent Number: 5,670,172

[45] Date of Patent: *Sep. 23, 1997

[54] PHARMACEUTICAL SPHEROID FORMULATION

[75] Inventors: Ian Richard Buxton; Helen Critchley; Stewart Thomas Leslie; Derek Allan Prater, all of Cambridge, United Kingdom; Ronald Brown Miller, Basel, Switzerland; Sandra Therese Antoinette Malkowska, Cambridge, United Kingdom

[73] Assignee: Euro-Celtique, S.A., Luxembourg, Luxembourg

[*] Notice: The term of this patent shall not extend beyond the expiration date of Pat. No. 5,601,845.

[21] Appl. No.: 426,065

[22] Filed: Apr. 21, 1995

Related U.S. Application Data

[63] Continuation of Ser. No. 926,501, Aug. 5, 1992, abandoned.

[30] Foreign Application Priority Data

Aug. 12, 1991 [GB] United Kingdom ............... 911761
Oct. 29, 1991 [GB] United Kingdom ............... 9122967

[51] Int. Cl.⁶ ............................ A61K 9/16; A61K 47/38
[52] U.S. Cl. .................... 424/495; 424/494; 424/497; 424/498; 424/499; 514/781
[58] Field of Search ........................ 424/495, 499, 424/497, 498, 494; 428/402; 514/781, 951

[56] References Cited

U.S. PATENT DOCUMENTS

| | | | |
|---|---|---|---|
| 4,456,628 | 6/1984 | Bauer et al. | 424/495 |
| 4,721,619 | 1/1988 | Panoz et al. | 424/459 |
| 4,808,413 | 2/1989 | Joshi et al. | 424/458 |
| 4,894,240 | 1/1990 | Geoghegan et al. | 424/497 |
| 4,917,899 | 4/1990 | Geoghegan et al. | 424/461 |
| 4,917,900 | 4/1990 | Junes et al. | 424/493 |
| 4,960,596 | 10/1990 | Debregeas et al. | 424/458 |
| 5,002,776 | 3/1991 | Geoghegan et al. | 424/497 |
| 5,112,621 | 5/1992 | Stevens et al. | 424/497 |
| 5,219,621 | 6/1993 | Geoghegan et al. | 424/462 |
| 5,286,497 | 2/1994 | Hendrickson et al. | 424/489 |
| 5,364,620 | 11/1994 | Geoghegan et al. | 424/462 |

FOREIGN PATENT DOCUMENTS

| | | | |
|---|---|---|---|
| 615221 | 6/1989 | Australia | A61K 9/24 |
| 3227389 | 10/1989 | Australia . | |
| 6798890 | 7/1991 | Australia . | |
| 634660 | 9/1991 | Australia | A61K 31/55 |
| 1327006 | 2/1994 | Canada | A61K 31/55 |
| 0149920 | 7/1985 | European Pat. Off. . | |
| 0154009 | 9/1985 | European Pat. Off. | A61K 31/54 |
| 0288732 | 11/1988 | European Pat. Off. . | |
| 0315414 | 5/1989 | European Pat. Off. . | |
| 0317855 | 5/1989 | European Pat. Off. | A61K 31/54 |
| 0322277 | 6/1989 | European Pat. Off. . | |
| 0320097 | 6/1989 | European Pat. Off. | A61K 31/55 |
| 0340105 | 11/1989 | European Pat. Off. . | |
| 0373417 | 6/1990 | European Pat. Off. | A61K 9/20 |
| 0163000 | 4/1991 | European Pat. Off. | A61K 9/52 |
| 0106443 | 7/1991 | European Pat. Off. | A61K 9/22 |
| 0446753 | 9/1991 | European Pat. Off. . | |
| 0327086 | 5/1992 | European Pat. Off. | A61K 9/54 |
| 0514814 | 11/1992 | European Pat. Off. | A61K 9/50 |
| 0220670 | 1/1993 | European Pat. Off. | A61K 9/54 |
| 56999 | 3/1992 | Ireland | A61K 9/52 |
| CH662507 | 10/1987 | Switzerland | A61K 31/38 |
| 2179251 | 8/1989 | United Kingdom | A61M 31/00 |
| 2227172 | 7/1990 | United Kingdom | A61K 31/55 |
| 2209280 | 9/1991 | United Kingdom | A61K 9/52 |
| 8802253 | 4/1988 | WIPO . | |
| 8908448 | 9/1989 | WIPO | A61K 9/52 |
| 9101722 | 2/1991 | WIPO . | |

OTHER PUBLICATIONS (Abstract), *Pharmaceuticals*, p. 8, Week K23, Abstract #54403 K/23 (EP–80–341), "Pharmaceutical multiple units formulation –with enterically coated cores for reduced peak plasma drug concentration", Benzon A AS.

(Abstract) *Pharmaceuticals*, Week K25, Abstract #59112 K/25 (EP–81–006), "Composition of beta–adrenergic blocer and tetra–hydro–benzazepine –useful as atihypertensive and in improving efficiency of kidney function", Alcide Co. Ltd. Partn (ALLI).

(Abstract) *Pharmaceuticals*, p. 3, Week 8407, Abstract #84–038350/07 (EP–100–061–A), "Pharmaceutical dosage units with enhanced bio:availability –especially hydro:chloro:thiazide–triameterene mixtures for uniform absoprtion", Mylan Pharm, Inc.

(Abstract) *Pharmaceuticals*, p. 6, Week 8528, Abstract #85–166500/28 (EP–147–780–A), "Pharmaceutical composition for oral, rectal or vaginal administration –with polvinyl alcohol film coating for controlled and prolonged release", (Merck & Co., Inc.

(Abstract) No. 22342C/13 (EP–9–657), "Diuretic compositions containing potassium retaining agents –comprising 2,4–di:amino–5–aminobenzl–pyrimidine derivatives", Hoffman–LaRoche AG.

(Abstract) No. 1593062, "Pharmaceutical controlled release compositions", 16 Sep. 1977, Richter Gedeon Vegyeszeti Gyar RT.

(Abstract), No. 85–184021/31 (EP–154–009–A), "Treatment of hypertension in patent –by administration of thiazide diuretic at level to cause antihypetensive action with diuresia", Euro–Celtique, S.A.

(Abstract), No. 89–158961/22 (EP–317–855–A), "Combination of moxonidine, hydro:chloro:thiazide and opt. triamteren –for long–term treatment of hypertonia and oedemas", Beiersdorf AG.

Primary Examiner—Edward J. Webman
Attorney, Agent, or Firm—Steinberg, Raskin & Davidson, P.C.

[57] ABSTRACT

A controlled release composition including spheroid cores of diltiazem or a pharmaceutically acceptable salt thereof and optionally a spheronizing agent, the cores being coated with a controlled release layer, and a method of manufacturing the same, is disclosed. The spheronizing agent when present is preferably microcrystalline cellulose. Ethylcellulose is a preferred release coating. The controlled release coating preferably contains a plasticizer, a surfactant and a tack-modifier.

21 Claims, No Drawings

PHARMACEUTICAL SPHEROID FORMULATION

This is a continuation of application Ser. No. 07/926,501, filed Aug. 5, 1992, abandoned the contents of which are incorporated herein in its entirety.

BACKGROUND OF THE INVENTION

The present invention relates to a controlled release preparation and to a process for its preparation. In particular it relates to a controlled release preparation containing diltiazem.

Diltiazem is a calcium antagonist which has been shown to be useful in treating chronic heart disease such as hypertension and angina.

OBJECTS AND SUMMARY OF THE INVENTION

It is an object of the present invention to provide a controlled release diltiazem preparation suitable for once daily administration for the treatment of hypertension and angina.

In view of the above object and others, the present invention is related to a controlled release composition comprising spheroid cores comprising diltiazem or a pharmaceutically acceptable salt thereof in an amount effective to render a therapeutic effect, and optionally a spheronizing agent, the cores being coated with a controlled release material in an amount effective to provide a controlled release of diltiazem when said composition is exposed to aqueous solutions.

In certain preferred embodiments of the present invention, the controlled release layer is provided in an amount suitable to provide a once daily dosage regimen.

The present invention is also related to a process for preparing a controlled release oral dosage preparation of diltiazem, comprising (a) granulating a mixture comprising diltiazem, or a pharmaceutically acceptable salt thereof with water and optionally a spheronizing agent; (b) extruding the granulated mixture to obtain an extrudate; (c) spheronizing the extrudate until spheroid cores are formed; (d) drying the spheroid cores; and (e) coating the spheroid cores with a controlled release material. Thereafter, the coated spheroid cores are filled into capsules or sachets or compressed into tablets in an amount effective to provide a therapeutic dosage of diltiazem when ingested orally by a patient.

In a preferred embodiment of the present invention, the resultant controlled release formulation of diltiazem is a one-a-day dosage.

DETAILED DESCRIPTION

Diltiazem is a calcium antagonist (calcium channel blocker) commonly available as the hydrochloride salt and having the chemical name 1,5-Benzothiazepin-4(5H)one,3-(acetyloxy)-5-[2-(dimethylamino)-ethyl]-2,3-dihydro-2-(4-methoxyphenyl)-, monohydrochloride, (+) -cis-.

Suitable pharmaceutically acceptable salts of diltiazem for use according to the present invention include pharmaceutically acceptable acid addition salts. The hydrochloride salt is particularly preferred.

A controlled release pharmaceutical composition according to the present invention is one that achieves slow release of a drug over an extended period of time and extends the duration of drug action over that achieved by conventional delivery.

The term "spheroid" is conventional in the pharmaceutical art and means a spherical granule having a diameter of between 0.1 mm and 2.5 mm, especially between 0.5 mm and 2 mm.

The spheroid cores for use according to the present invention preferably contain from about 40% to about 98%, more preferably from about 60% to about 85%, and most preferably from about 70% to about 85% by weight of diltiazem or its pharmaceutically acceptable salts.

The spheronizing agent may comprise any pharmaceutically acceptable material which may be spheronized together with the active ingredient to form spheroid cores. A preferred spheronizing agent is microcrystalline cellulose. The microcrystalline cellulose employed may be, for example, Avicel PH 101 or Avicel PH 102 (™FMC Corporation). Conveniently the spheronizing agent, when present, is present in an amount of from 1% to 60%, and preferably from 15% to 40%, by weight of the spheroid cores.

Optionally, the spheroid cores may also contain other pharmaceutically acceptable excipients and diluents which facilitate spheronization such as pharmaceutically acceptable sugars (for example sucrose, dextrose, maltose or lactose) or pharmaceutically acceptable sugar alcohols (for example mannitol, xylitol or sorbitol). Colorants may also be included in the spheroid core.

The spheroid cores are coated with a material which permits release of the diltiazem at a controlled rate in an aqueous medium. Suitable controlled release coating materials include those well known in the art such as water insoluble waxes and polymers such as polymethacrylates (for example, Eudragit polymers™) or, preferably, water insoluble celluloses (for example, alkylcelluloses such as ethylcellulose). The coating may also include water soluble polymers such as polyvinylpyrrolidone or, preferably, a water soluble cellulose such as hydroxypropylmethylcellulose and/or hydroxypropylcellulose. It will be appreciated that the ratio of water insoluble to water soluble material will depend on the release rate required and the solubility of the materials selected. The ratio of water soluble polymer to water insoluble polymer is preferably from about 1:20 to about 1:2.

The controlled release coating preferably includes one or more pharmaceutically acceptable plasticizers conventional in the art such as diethylphthalate, or, preferably, dibutyl sebacate; surfactants such as sorbitan trioleate, sorbitan monolaurate, or, preferably, polysorbate 80 (Tween 80™); and tack-modifiers, such as talc, or, preferably, colloidal anhydrous silica.

The amount of plasticizer, when present, will depend on the particular plasticizer selected. In general, the plasticizer is present in an amount from about 1% to about 25% by weight of the controlled release film coat. The surfactant, when present, is suitably present in an amount from about 1% to about 25% by weight of the controlled release film coat. The tack-modifier, when present, is also suitably present in an amount from about 1% to about 25% by weight of the controlled release film coat.

A preferred controlled release film coating in accordance with the present invention comprises from about 50% to about 95% ethylcellulose, from about 5% to about 15% colloidal anhydrous silica, from about 5% to about 15% dibutyl sebacate, and from about 5% to about 15% polysorbate 80 (Tween 80™).

The controlled release film coating layer can be formed on the surface of the diltiazem-containing spheroid cores using conventional coating methods, for example fluidized bed or pan coating. The coating materials may be applied as a solution or suspension. Suitable solvent systems include water, dichloromethane, ethanol, methanol, isopropyl alcohol and acetone mixtures thereof, and the like. The coating solution or suspension preferably contains from about 2% to about 60%, and preferably from about 2% to about 20% by weight of coating materials.

The amount of the controlled release coating material applied onto the spheroid cores will depend on the desired release rate. Generally, the amount of the controlled release coating material in the formulation is in the range of from about 1% to about 25%, and preferably from about 2% to about 8%, by weight of the composition.

The controlled release composition according to the invention may be prepared by (a) granulating a mixture comprising diltiazem or a pharmaceutically acceptable salt thereof, water and optionally a spheronizing agent;

(b) extruding the granulating mixture to give an extrudate;

(c) spheronizing the extrudate until spheroid cores are formed; and (d) film-coating the spheroid cores with a controlled release coating.

Compositions according to the invention may be filled into capsules or sachets or compressed into tablets using conventional pharmaceutical techniques.

In a preferred embodiment, the composition according to the present invention may be orally administered once daily. Conveniently, for once daily administration the dosage form contains from 120 mg to 300 mg to diltiazem or a pharmaceutically acceptable salt thereof, preferably diltiazem hydrochloride.

DETAILED DESCRIPTION OF THE PREFERRED EMBODIMENTS

The following examples illustrate various aspects of the present invention. They are not to be construed to limit the claims in any manner whatsoever.

EXAMPLE 1

In Example 1, diltiazem capsules were prepared in accordance with the present invention. First, diltiazem hydrochloride and microcrystalline cellulose were blended using a high shear mixer. The mixture was wet granulated, and extruded to give an extrudate which was spheronized and dried in a fluid bed drier. The spheroids were sieved to give a particle size of 0.85 to 1.7 mm. The diltiazem spheres had the composition set forth in Table 1 below:

TABLE 1

| Diltiazem Spheroid Cores | |
|---|---|
| Material | mg |
| Diltiazem hydrochloride U.S.P. | 120 |
| microcrystalline cellulose E.P. (Avicel PH101) | 30.0 |
| Purified water E.P. | q.s. |
| Total | 150 |

The controlled release film coating ingredients, ethylcellulose, colloidal anhydrous silica, dibutyl sebacate, and polysorbate 80, were dispersed in a dichloromethane/methanol solvent system. The amounts of the above materials used to prepare the coating are set forth in Table 2 below:

TABLE 2

| Controlled Release Film Coat | |
|---|---|
| Material | mg |
| Diltiazem hydrochloride spheroid core | 150 |
| Ethylcellulose N10 U.S.N.F. | 7.38 |
| Colloidal anhydrous silica E.P. (Aerosil 130) | 0.988 |
| Dibutyl sebacate U.S.N.F. | 0.742 |
| Polysorbate 80 E.P. (Tween 80) | 0.791 |
| Dichloromethane BS 1994 | q.s. |
| Methanol B.P. 1973 | q.s. |
| Total | 160 |

The controlled release film coat was then applied to the diltiazem spheroid cores in a fluid bed coater. The resulting film coated spheroids were sieved. The coated spheroids were filled into gelatin capsule shells. Further information is provided in Table 3 below:

TABLE 3

| Capsule formulation | |
|---|---|
| Material | mg |
| Diltiazem controlled release spheroids | 160 |
| Magnesium stearate E. P. | 0.480 |
| Gelatin capsule shells size | 3 |

The resulting capsule were thereafter subjected to dissolution testing measured by E.P. basket apparatus at 100 rpm in a pH 4.5 E.P. phosphate buffer. The results obtained are recorded in Table 4 below:

TABLE 4

| Diltiazem Dissolution | |
|---|---|
| Time (hours) | Percent Diltiazem Released |
| 1 | 9 |
| 2 | 23 |
| 3 | 37 |
| 4 | 48 |
| 5 | 57 |
| 6 | 63 |
| 8 | 72 |
| 10 | 77 |
| 12 | 81 |
| 15 | 86 |
| 20 | 90 |

The examples provided above are not meant to be exclusive. Many other variations of the present invention would be obvious to those skilled in the art, and are contemplated to be within the scope of the appended claims.

What is claimed is:

1. A once a day controlled release composition comprising spheroid cores consisting essentially of diltiazem or a pharmaceutically acceptable salt thereof in an mount of about 40–98% by weight and being sufficient to provide a therapeutic effect over a one day period, and about 2–60% by weight of microcrystalline cellulose, said cores being with a water insoluble pharmaceutically acceptable controlled release material consisting of ethyl cellulose in an mount effective to provide a controlled release of diltiazem throughout a one day period when said composition is exposed to aqueous solutions, said controlled release material being present in an amount of from about 1% to about 25% by weight of said composition.

2. The process according to claim 1 wherein the spheroid cores comprise from about 70% to about 85% by weight diltiazem or a pharmaceutically acceptable salt thereof.

3. The composition according to claim 1 wherein the spheronizing agent is present in an amount from about 15% to about 40% by weight of the spheroid cores.

4. The composition according to claim 1 wherein the spheronizing agent comprises microcrystalline cellulose.

5. The composition according to claim 1 wherein the controlled release coating material is present in an amount of from about 2% to about 8% by weight of the composition.

6. A capsule comprising controlled release coated spheroid cores according to claim 1.

7. A once a day controlled release composition comprising spheroid cores consisting essentially of diltiazem or a pharmaceutically acceptable salt thereof in an mount of about 40-98% by weight and being sufficient to provide a therapeutic effect over a one day period, and about 2-60% by weight of microcrystalline cellulose, said cores being coated with a water insoluble pharmaceutically acceptable controlled release material selected from the group consisting of a plasticizer, a surfactant, a tack-modifier, and a mixture of any of the foregoing, said controlled release material being present in an amount of from about 1% to about 25% by weight of said composition.

8. The composition according to claim 7 wherein the controlled release coating comprises from about 50% to about 95% ethylcellulose, from about 5% to about 15% dibutyl sebacate and from about 5% to about 15% polysorbate 80.

9. A process for preparing a solid controlled release oral once a day dosage formulation of diltiazem, comprising
   (a) granulating a mixture comprising diltiazem or a pharmaceutically acceptable salt thereof in an amount of about 40-98% by weight, water and about 2-60% by weight of microcrystalline cellulose;
   (b) extruding the granulating mixture to give an extrudate;
   (c) spheronizing the extrudate until spheroid cores are formed;
   (d) drying the spheroid cores; and
   (e) coating a sufficient amount of spheroid cores to provide a one a day dosage with a water insoluble pharmaceutically acceptable controlled release material consisting of ethylcellulose in an amount of from about 1% to about 25% by weight of said formulation and sufficient to provide controlled release of the diltiazem throughout a one day period.

10. The process according to claim 9, further comprising filing an effective amount of said coated spheroid cores to provide a therapeutic effect into a capsule or sachet.

11. The process according to claim 9, further comprising compressing an effective amount of said coated spheroid cores to provide a therapeutic effect into a tablet.

12. A once a day controlled release composition comprising spheroid cores consisting essentially of a mixture of diltiazem or a pharmaceutically acceptable salt thereof in an amount of about 40-98% by weight and being sufficient to provide a therapeutic effect over a one day period, and about 2-60% by weight of microcrystalline cellulose, said cores being coated with a pharmaceutically acceptable controlled release coating consisting essentially of an effective amount of ethylcellulose to provide a controlled release of diltiazem over a one day period when said composition is exposed to aqueous solutions, and effective amounts of a plasticizer, a surfactant, a tack-modifier and mixtures thereof, said controlled release coating being present in an amount of from about 1% to about 25% by weight of said composition.

13. The composition according to claim 12 further wherein said tack modifier is present in an amount ranging from about 1% to about 25% by weight relative to the controlled release film.

14. The composition according to claim 12 wherein the spheroid core consists of from about 70% to about 85% by weight diltiazem or a pharmaceutically acceptable salt.

15. The composition according to claim 12 wherein the spheroid cores consist of from about 70% to about 85% by weight diltiazem or a pharmaceutically acceptable salt thereof.

16. The composition according to claim 12 wherein the spheronizing agent is present in an amount from about 15% to about 40% by weight of the spheroid cores.

17. The composition according to claim 12 wherein the spheronizing agent is microcrystalline cellulose.

18. The composition according to claim 17 further wherein said tack modifier is present in an amount ranging from about 1% to about 25% by weight relative to the controlled release film.

19. The composition according to claim 12 wherein the controlled release coating material consists essentially of from about 50% to about 95% ethylcellulose, from about 5% to about 15% dibutyl sebacate and from about 5% to about 15% polysorbate 80.

20. The composition according to claim 12 wherein the controlled release coating is present in an amount of from about 2% to about 8% by weight of the composition.

21. A capsule comprising controlled release coated spheroid cores according to claim 12.

* * * * *